(12) United States Patent
Wasicek (10) Patent No.: US 7,245,959 B1
(45) Date of Patent: Jul. 17, 2007

(54) IMAGING CATHETER FOR USE INSIDE A GUIDING CATHETER

(75) Inventor: Lawrence Wasicek, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 9 days.

(21) Appl. No.: 09/798,563

(22) Filed: Mar. 2, 2001

(51) Int. Cl.
 *A61B 5/05* (2006.01)
 *A61B 8/12* (2006.01)

(52) U.S. Cl. .................................. 600/407; 600/466

(58) Field of Classification Search ............... 600/460, 600/459, 461, 407, 424, 462–471; 604/93.01, 604/95.03–95.04, 103.04, 103.09, 164.13, 604/171
See application file for complete search history.

(56) References Cited

U.S. PATENT DOCUMENTS

| 4,464,176 A | | 8/1984 | Wijayarathna | |
|---|---|---|---|---|
| 4,580,551 A | | 4/1986 | Siegmund et al. | |
| 4,665,925 A | * | 5/1987 | Millar | 604/96 |
| 4,739,768 A | * | 4/1988 | Engelson | 600/435 |
| 4,817,613 A | | 4/1989 | Jaraczewski et al. | 128/658 |
| 4,917,097 A | * | 4/1990 | Proudian et al. | 600/466 |
| 4,979,939 A | * | 12/1990 | Shiber | 606/159 |
| 5,024,234 A | | 6/1991 | Leary et al. | 128/663.01 |
| 5,095,911 A | | 3/1992 | Pomeranz | 128/662.06 |
| 5,174,295 A | | 12/1992 | Christian et al. | |
| 5,203,338 A | * | 4/1993 | Jang | 600/463 |
| 5,324,259 A | * | 6/1994 | Taylor et al. | 604/99.04 |
| 5,357,978 A | * | 10/1994 | Turk | 600/585 |
| 5,368,035 A | * | 11/1994 | Hamm et al. | 600/466 |
| 5,400,789 A | * | 3/1995 | Griffith | 600/466 |
| 5,421,338 A | * | 6/1995 | Crowley et al. | 600/463 |
| 5,451,233 A | * | 9/1995 | Yock | 606/194 |
| 5,531,700 A | * | 7/1996 | Moore et al. | 604/164.13 |
| 5,531,719 A | * | 7/1996 | Takahashi | 604/525 |
| 5,571,056 A | | 11/1996 | Kaplan et al. | |
| 5,715,825 A | * | 2/1998 | Crowley | 600/462 |
| 5,738,100 A | | 4/1998 | Yagami et al. | 128/662.06 |
| 5,762,631 A | * | 6/1998 | Klein | 604/171 |
| 5,772,642 A | * | 6/1998 | Ciamacco et al. | 604/623 |
| 5,833,706 A | * | 11/1998 | St. Germain et al. | 606/194 |
| 5,865,178 A | | 2/1999 | Yock | |
| 5,879,305 A | * | 3/1999 | Yock et al. | 600/462 |
| 5,895,397 A | | 4/1999 | Jang et al. | |
| 5,902,245 A | * | 5/1999 | Yock | 600/463 |
| 5,931,797 A | | 8/1999 | Dietz et al. | |
| 5,938,609 A | | 8/1999 | Pomeranz | 600/439 |
| 6,004,291 A | * | 12/1999 | Ressemann et al. | 604/96.01 |

(Continued)

FOREIGN PATENT DOCUMENTS

WO WO 98/46119 A1 10/1998

(Continued)

Primary Examiner—Francis J. Jaworski
(74) Attorney, Agent, or Firm—Orrick Herrington & Sutcliffe LLP (57) ABSTRACT

An imaging catheter which is constructed to be inserted into a guiding catheter having a small outer diameter, such as 5 French, such that a standard guidewire and imaging catheter are simultaneously translatable through a lumen of the guiding catheter. The imaging catheter includes an elongated tubular member and a cover tube made from materials which allow the outer diameter of the imaging catheter to be reduced sufficiently to fit within the small guiding catheter without sacrificing imaging quality.

24 Claims, 5 Drawing Sheets

U.S. PATENT DOCUMENTS 6,083,152 A     7/2000  Strong
6,165,127 A *  12/2000  Crowley ..................... 600/439
6,210,396 B1 *  4/2001  MacDonald et al. ........ 604/529
6,234,971 B1    5/2001  Jang .......................... 600/462
6,413,222 B1 *  7/2002  Pantages et al. ............ 600/466
6,626,816 B1 *  9/2003  Ciezki et al. ................. 600/3
6,635,027 B1 * 10/2003  Cragg et al. ................. 604/22

FOREIGN PATENT DOCUMENTS

WO      WO 99/49793 A1    10/1999

* cited by examiner

IMAGING CATHETER FOR USE INSIDE A GUIDING CATHETER

FIELD OF THE INVENTION

The present invention relates generally to the field of imaging catheters, and in particular, to an imaging catheter that can be used inside a guiding catheter which preferably has a small outer diameter such as a 5 French guiding catheter.

BACKGROUND OF THE INVENTION

Imaging catheters are used in conjunction with guiding catheters to access and map a patient's vascular system. The purpose of the guiding catheter is to more effectively introduce the imaging catheter into the vascular system. The guiding catheter is typically inserted percutaneously into the patient's arterial system through the femoral artery in the groin. With the aid of a guidewire, the guiding catheter is advanced through the patient's vascular system.

Once the guiding catheter is in place, the imaging catheter is introduced into the guiding catheter alongside the guidewire. Such imaging catheters, also known as intravascular ultrasound (IVUS) catheters, have an ultrasonic imaging element attached at the distal end of the catheter for producing cross-sectional images of the vessel. Because the guidewire and imaging catheter are to be employed within the guiding catheter at the same time, the inner diameter of the guiding catheter must be at least as large as the sum of the outer diameters of the guidewire and imaging catheter.

Since prior art imaging catheters have relatively large outer diameters, they are not compatible with smaller guiding catheters, such as 5 French guiding catheters. This incompatibility is a problem since accessing smaller coronary vessels may require the use of a 5 French guiding catheter, and ultrasound imaging would, therefore, be impossible.

It would therefore be desirable to provide an improved imaging catheter having a reduced outer diameter such that the imaging catheter would be compatible with a smaller guiding catheter, such as a 5 French guiding catheter.

SUMMARY OF THE INVENTION

A first, separate aspect of the invention involves a catheter system comprising a small guiding catheter such as a 5 French guiding catheter, an imaging catheter and a guidewire, wherein the imaging catheter and guidewire are simultaneously translatable through the lumen of the 5 French guiding catheter. The imaging catheter includes an elongate tubular member having a proximal end, a distal end, a lumen and a cover tube laminated over the elongated tubular member.

A second, separate aspect of the invention involves a catheter system comprising a small guiding catheter such as a 5 French guiding catheter, an imaging catheter and a guidewire, wherein the imaging catheter includes an elongated tubular member is made from resins selected from the group consisting of polyetheretherketon, polyimide, braided coiled composites and hypo tubes. The imaging catheter further includes a cover tube formed from materials selected from the group consisting of polyethylene, urethane and PEBAX™.

A third, separate aspect of the invention involves a catheter system comprising a small guiding catheter such as a 5 French guiding catheter, an imaging catheter and a guidewire, wherein the outer diameter of the imaging catheter is less than about 0.044 inches, the outer diameter of the guidewire is about 0.014 inches and the inner diameter of the guiding catheter is about 0.058 inches.

A fourth, separate aspect of the invention involves a catheter system comprising a small guiding catheter such as a 5 French guiding catheter, an imaging catheter and a guidewire, wherein the imaging catheter includes an acoustic imaging window (preferably, dome-shaped) attached at the distal end of the elongate tubular element using, for example, a low profile thermal bond, wherein the acoustic imaging window is formed from materials selected from the group consisting of methylpentene copolymer, polyethylene, urethane and PEBAX™.

A fifth, separate aspect of the invention involves an imaging catheter including a rotatable imaging core adapted to pass through the lumen of the imaging catheter, the imaging core including a flexible drive-shaft and a transducer element comprising a cylinder, preferably disk-shaped. The imaging core further includes a transducer housing having a cut-away portion which slopes at an angle with respect to the central axis of the drive-shaft, wherein the transducer is mounted in the cut-away portion such that it slopes at an angle with respect to the central axis of the drive-shaft.

A sixth, separate aspect of the invention involves a catheter system comprising a small guiding catheter such as a 5 French guiding catheter, an imaging catheter and a guidewire, wherein an acoustic imaging window is located at a distal tubular portion of the imaging catheter, proximal from a distal tip of the imaging catheter. The distal tip of the imaging catheter is comprised of a flexible section having an angled slot or groove extending continuously through at least five rotations, wherein the width of the slot varies along the length of the slot whereby the width of the slot is less in proximal portions of the slot relative to distal portions thereof. Alternatively, the distal tip may have a tapered distal extremity or duck bill for atraumatic insertion into the body.

The invention may include any one of these separate aspects individually, or any combination of these separate aspects.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The drawings illustrate the design and utility of preferred embodiments of the invention. The components in the drawings are not necessarily to scale, emphasis instead being placed upon illustrating the principles underlying the embodiment. Moreover, in the drawings, like reference numerals designate corresponding parts throughout the different views.

DESCRIPTION OF THE PREFERRED EMBODIMENT

Figure 1:
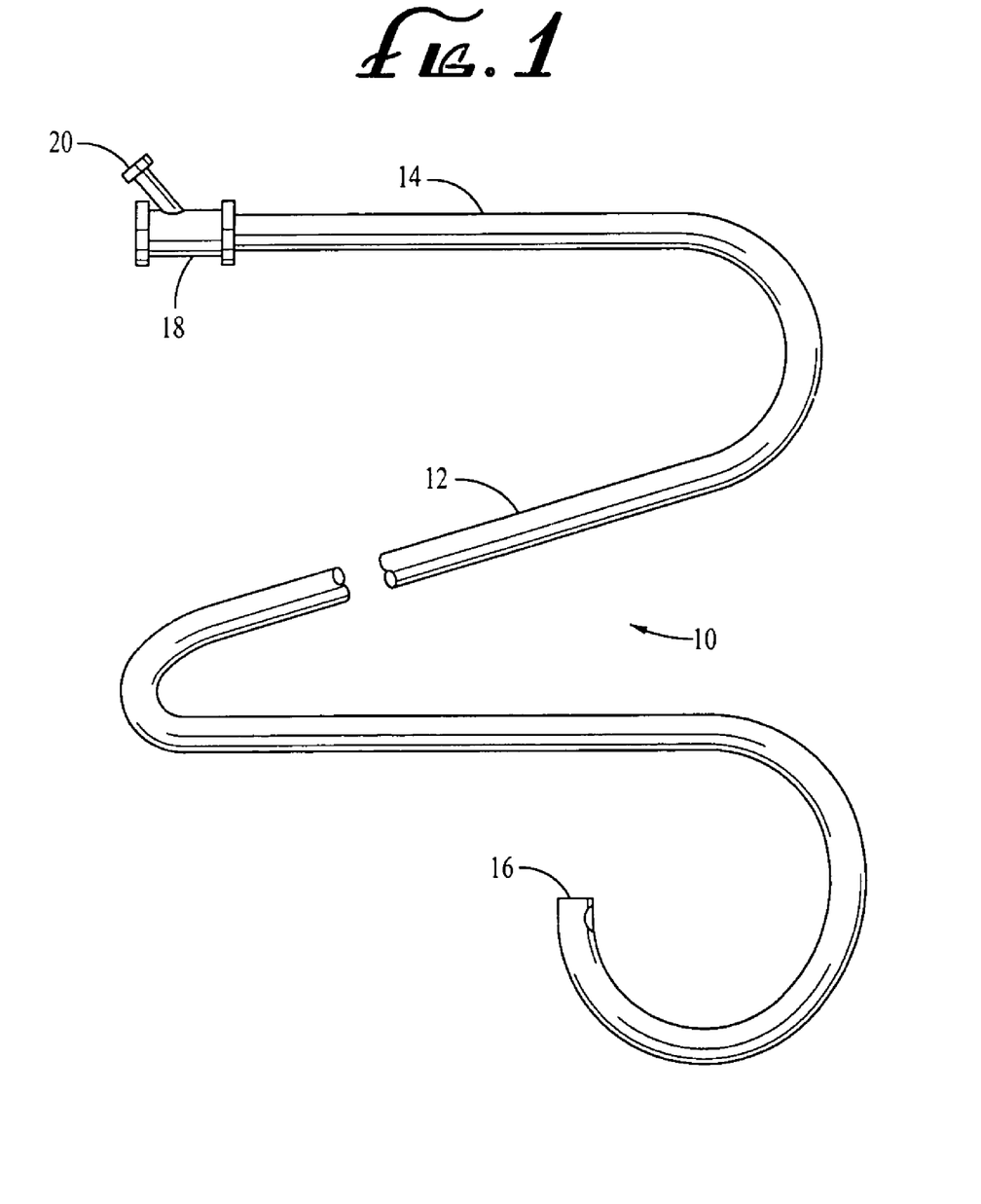
FIG. 1 shows an exemplary embodiment of a guiding catheter.

Referring now to FIG. 1, an exemplary embodiment 10 of the guiding catheter will be described. The guiding catheter 10 includes tubular flexible catheter body 12 having a proximal end 14 and a distal end 16. A proximal housing 18 having a hemostasis valve is generally secured to the proximal end 14 of the catheter body 12 and includes a side port 20 for injecting fluids, such as saline and contrast media, into the guiding catheter 10. Guiding catheter 10 is preferably a standard 5 French guiding catheter having a lumen diameter of about 0.058 inches.

The tube of the guiding catheter may be composed of a wide variety of biologically compatible materials, typically being made from natural or synthetic polymers, such as silicone, rubber, natural rubber, polyethylene, polyvinylchloride, polyurethanes, polyesters, polytetrafluoroethylenes (PTFE) and the like. Particular techniques for forming the guiding catheters out of such materials are well known in the art.

Ultrasonic imaging catheters are also well known in the art and usually employ an ultrasonic transducer mounted within a distal end of a catheter body. These imaging catheters are arranged to admit and receive ultrasonic energy within an imaging plane disposed normal to the axial direction of the catheter. During use, an external motor powers a drive-shaft, which causes a mechanical rotation of the ultrasonic image transducer about the imaging plane to produce a cross-sectional image of the imaging site. The images are preferably displayed on a monitor screen so that a physician can view the vascular system while performing the procedure.

Figure 2:
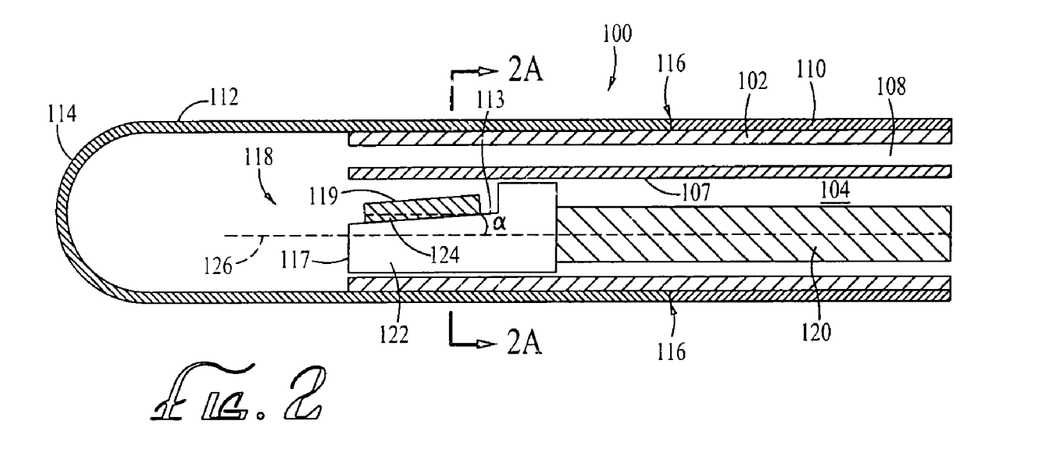
FIG. 2 shows a cut-away partial side view of an exemplary embodiment of an imaging catheter.
Figure 2A:
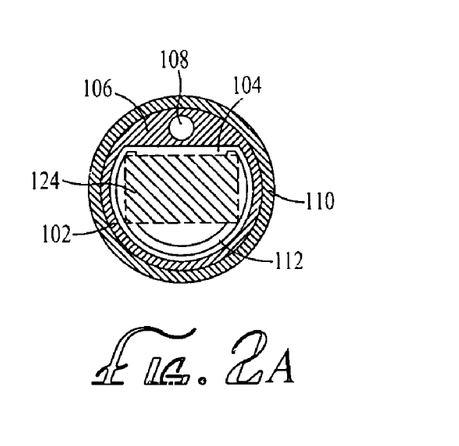
FIG. 2A shows a cross-sectional view of the imaging catheter of FIG. 2 taken along line 2A—2A.

FIGS. 2 and 2A illustrate an exemplary embodiment of a flexible ultrasound imaging catheter 100. Imaging catheter 100 is adapted to be positioned within the vascular system by standard, well-known catheter procedures by guiding the flexible imaging catheter 100 through various blood vessels along a circuitous path, beginning, for example, by percutaneous introduction through a perforation of the femoral artery.

The catheter includes an elongate tubular member 102 that forms a lumen 104 having inner dimensions sufficient to allow an imaging core 118 to be slidably disposed therein. The imaging core includes a flexible drive-shaft 120 connected to a transducer housing 122 having a transducer 124 mounted therein. Preferably, transducer 124 is generally disk-shaped. The imaging core 118 is capable of translation along its central axis. In addition, imaging core 118 is capable of rotation about its central axis at speeds in excess of, for example, 1800 rpm. Further disclosure concerning rotatable, motor-driven imaging cores can be found in U.S. Pat. No. 6,004,269, the entire patent being incorporated herein by reference.

Elongate tubular member 102 includes a proximal end that is designed to have exceptionally thin walls without sacrificing stiffness. As discussed below, thin imaging catheter walls are necessary for compatibility with a small outer diameter catheter such as a 5 French guiding catheter. In addition, the tubular member 102 must be temperature, chemical and fatigue resistant, and must exhibit excellent flexural, impact and tensile characteristics. Suitable materials for tubular member 102 include, but are not limited to, engineering resins such as polyetheretherketon (PEEK), polyimide, braided coiled composites and hypo tubes. A cover tube 110 formed of a suitable material, such as polyethylene, urethane, PEBAX™ or other plastic, is laminated over tubular element 102, wherein cover tube 110 provides both structural integrity to the catheter 100, as well as a smooth outer surface for ease in axial movement in a patient's body passage with minimal friction.

An acoustic imaging window 112, which is preferably rounded, is attached to a distal end of the elongate tubular element 102, thereby forming an enclosed tip of the catheter 100. Acoustic imaging window 112 is preferably formed from materials such as polyethylene, which exhibits an excellent combination of transparency, imaging quality and resistance to heat and chemicals. Alternatively, acoustic imaging window 112 may be formed from other suitable thermoplastics such as polyethylene, urethane, TPX™ (methylpentene copolymer) or PEBAX™.

The acoustic imaging window 112 has its proximal end open and its distal end rounded and is attached to a distal outer circumferential portion of the tubular element 102 to form an enclosed catheter tip 114, with respective ends of the cover tube 110 and acoustic imaging window 112 bonded together at a common joint 116. In order to reduce the thickness of common joint 116, a low profile thermal bond is used to attach acoustic imaging window 112 to cover tube 110. The use of a low profile thermal bond significantly reduces common joint 116 thickness when compared to prior art lap joints such as adhesive lap joints and overlap joints The outer diameter of the proximal end of window 112 is substantially equal to that of the installed cover tube 110, so that a smooth outer surface is provided at joint 116. As best seen in FIG. 2, optional upper portion 106 of the elongate tubular member 102 forms a smaller lumen 108, which can be used for other catheter functions such as, by way of non-limiting examples, housing pullwires, drug delivery, balloon angioplasty, laser ablation, or for housing a stiffening member to help prevent the collapsing of the catheter 100. Of course, the catheter may have any number of lumens of any size, shape and configuration. The catheter could have a balloon or a plurality of balloons, if desired. The catheter could also have more than one window, wires embedded in the catheter walls, multiple transducers, or other features. For example, the catheter could use a multiple resonant frequency transducer. Optionally, the catheter could use a plurality of multiple resonant frequency transducers, or another transducer in addition to a multiple resonant frequency transducer.

With further reference to the particular example shown in FIG. 2, the transducer housing 122 has a longitudinally disposed cut-away portion 113, which preferably slopes at a slight angle, alpha, with respect to the central axis 126 of drive-shaft 120. The transducer 124 is mounted in the cut-away portion 113 of the transducer housing 122 such that its active surface 119 also slopes at angle alpha with respect to central axis 126 of drive-shaft 120. This tilting of transducer 124 helps to minimize internal reflections inside of catheter tip 114.

Although the preferred transducer 124 is disk-shaped, it may alternatively be any other shape. In use, it converts electrical energy pulses into mechanical energy, which propagates out from the face of the transducer 124 in the form of ultrasonic waves. The frequencies of these ultrasonic waves are dependent upon the excitation frequencies and the natural resonant frequencies of the transducer 124.

The natural resonant frequencies of the transducer 124 are a product of the shape and thickness of the transducer 123 and the transducer material. Transducer 124 is formed in a known manner from materials capable of transforming pressure distortions on its surface into electrical voltages and vice versa. Such materials include, but are not limited to, piezoelectric ceramic materials, piezocomposite materials, piezoelectric plastics, barium titanates, lead zirconate titanates, lead metaniobates and polyvinylidenefluorides.

Figure 3:
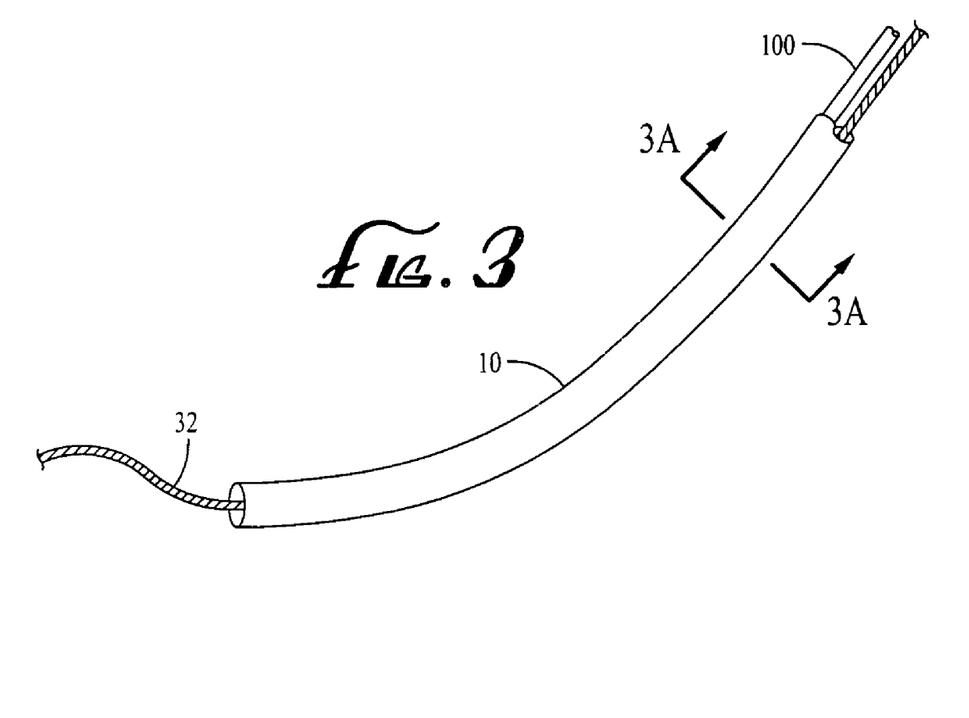
FIG. 3 shows an exemplary embodiment of the guiding catheter, imaging catheter and a guidewire.
Figure 3A:
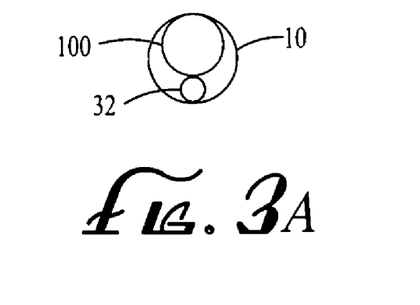
FIG. 3A shows a cross-sectional view of the guiding catheter, imaging catheter and guidewire of FIG. 3 taken along line 3A—3A.

Referring to FIGS. 3 and 3A, guiding catheter 10 is to be introduced and advanced through the vascular system in a known fashion. Once the guiding catheter 10 is in the desired position, a standard coronary guidewire 32 having a diameter of approximately 0.014 inches is inserted into the vascular system through the guiding catheter 10. Imaging catheter 100 is then introduced through the guiding catheter 10, typically adjacent to the guidewire 32. As mentioned previously, a state-of-the-art 5 French guiding catheter has a lumen diameter of about 0.058 inches. Therefore, the diameter of this example imaging catheter 100 must be less than or equal to approximately 0.044 inches (0.058–0.014) in order to fit adjacent to guidewire 32 within guiding catheter 10. Consequently, the improved imaging catheter 100 has been downsized such that its outer diameter is approximately 0.043 inches. As discussed above, the downsizing of imaging catheter 100 was made possible by the use of specific materials designed to allow thin catheter walls without sacrificing functionality.

Figure 4:
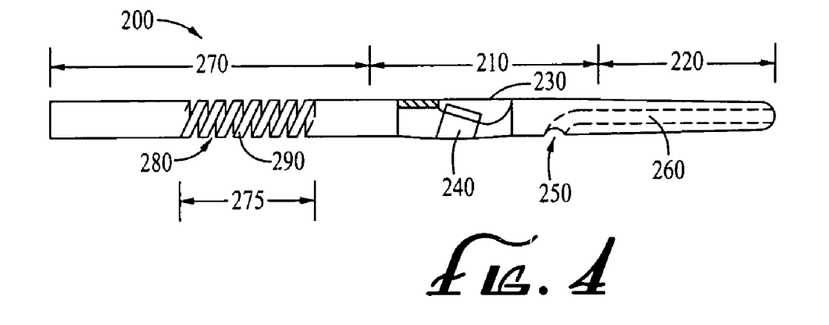
FIGS. 4–9 show additional embodiments of the imaging catheter.

Referring to FIG. 4, in an alternative preferred embodiment, imaging catheter 200 is located in distal tubular portion 210 instead of in the distal tip 220. Imaging window 230 allows the passage of ultrasonic sound waves emanating from ultrasound imaging transducer 240. Placing the transducer 240 in distal tubular portion 210 allows the distal tip 220 to serve other functions such as a passageway for guidewire 32. For example, distal tip 220 may include a guidewire port 250 and a guidewire lumen 260 dimensioned for the passage of guidewire 32.

In order to increase flexibility in proximal tubular portion 270, a slot 280 can be cut completely through wall 290 of proximal tubular portion 270 to form flexible section 275. Alternatively, to vary the stiffness of flexible section 275, a portion of slot 280 may be replaced with a grooved section (not shown), which is only partially cut through the wall of proximal tubular portion 270. In either embodiment, slot 280 preferably extends continuously for at least one rotation, preferably through a plurality of rotations, e.g., from about 3 to 15 rotations.

Figure 5:
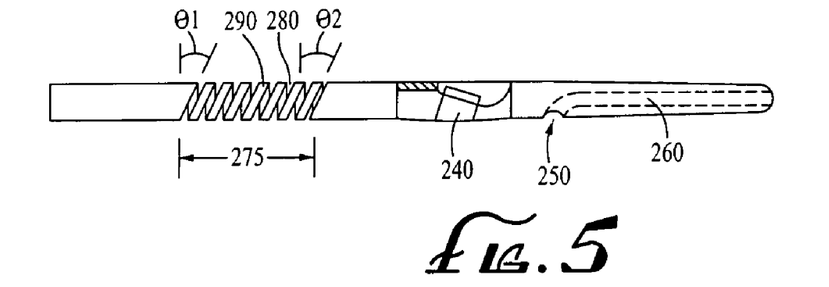

Referring to FIG. 5, to vary the stiffness within flexible section 275, oblique angle theta can be varied such it is greater at proximal portions of slot 280 than distal portions thereof, e.g., oblique angle theta, is greater than oblique angle $theta_2$. Additionally, the stiffness of flexible section 275 may be varied by increasing the width of slot 280 proximally to distally.

Figure 6:
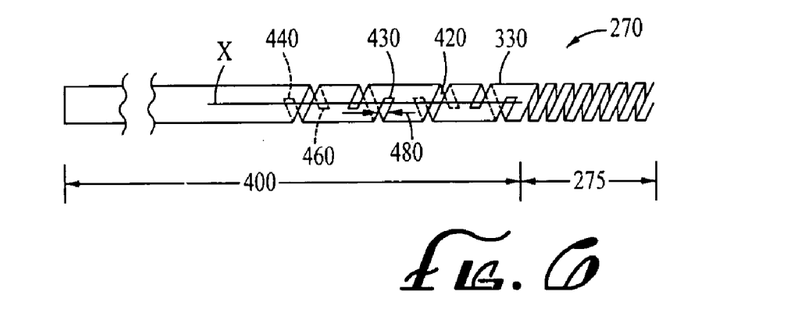

Referring now to FIG. 6, proximal tubular portion 270 may further comprise transition section 400, located proximally of flexible section 275. Portions of wall 330 in transition section 400 are removed to impart an intermediate range of flexibility to transition section 400. Wall 330 may be removed only partially, such as, for example, having a groove or a notch cut only partially through wall 330, or wholly, such as, for example, a slot cut completely through wall 330, or a combination of both.

Transition section 400 includes at least one discontinuous slot 420, and preferably a plurality of discontinuous slots 420, separated by unslotted portions 430 of wall 330. Discontinuous slot 420 is preferably generally helically aligned about wall 330 of proximal tubular portion 270 and proceeds through more than one rotation about proximal tubular portion 270. In particular, if a reference line "X" is drawn on wall 330 parallel to the longitudinal axis of proximal tubular portion 270, discontinuous slot 420, having one end 440 beginning on or near reference line "X", proceeds generally helically about proximal tubular portion 270 such that second end 460 is located past reference line "X", i.e., discontinuous slot 420 proceeds through more than one rotation about proximal tubular portion 270. The width 480 of slot 420 may be constant or may vary as described above.

Figure 7:
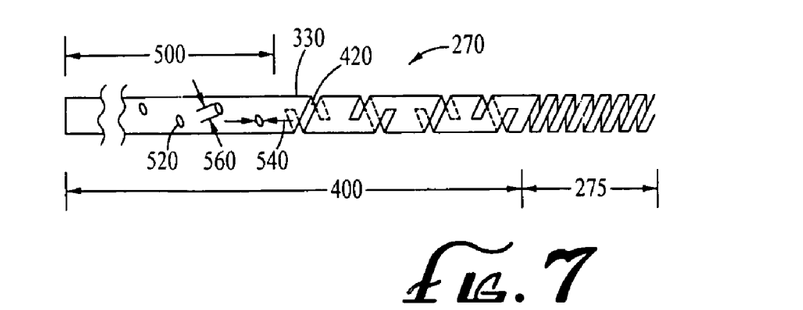

Referring to FIG. 7, transition section 400 may further comprise a pattern of perforations 500 through wall 330 of proximal tubular portion 270. The pattern size and shape of the perforations 500 are selected such that the pattern of perforations 500 is less flexible than discontinuous slots 420. The pattern of perforations 500 consists of a plurality of angled slots 520 that are cut through wall 330. Alternatively, angled slots 520 may be only partially cut through wall 330 and may have various depths to alter the stiffness of proximal tubular portion 270 at the pattern of perforations 500. Angled slots 520 are oriented at a particular pitch, preferably 45 degrees, and are disposed at 90 degree or 120 degree intervals along wall 330 of proximal tubular portion 270. The desired degree of flexibility in the pattern of perforations 500 may be varied by varying slot width 540, slot length 560, and the distance between slots. Additionally, the shape of angled slots 520 may be varied to vary the flexibility.

Proximal tubular portion 270 is preferably manufactured from a nitinol tube. To impart the desired flexibility characteristics to flexible section 300 and transition section 400, slots 320, 420, and 520 are formed into proximal tubular portion 270 by, for example, electrical discharge machining, chemical masking, electro-chemical etching, or laser etching.

Figure 8:
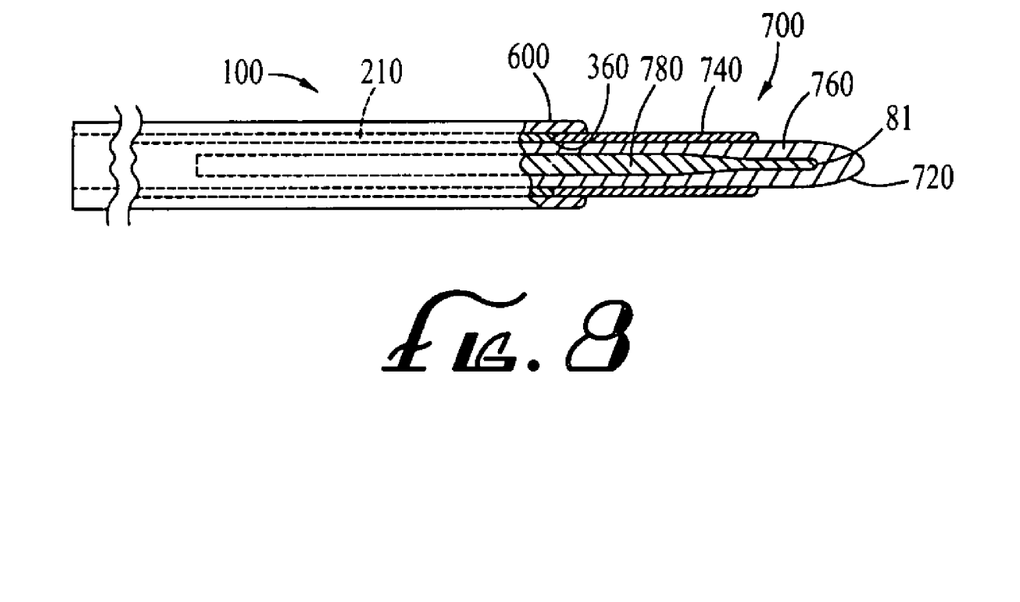

Referring to FIG. 8, in one embodiment, a distal tip portion 700 is bonded to a sealing element 600 on distal tubular portion by, for example, a flexible adhesive, such as urethane. To enable atraumatic insertion of imaging catheter 100 into the body, distal tip portion 700 is flexible and has a tapered distal extremity 720. Distal tip portion 700 may include sleeve 740, which abuts distal end 360 of distal tip portion 210. Sleeve 740 further surrounds core 760, which encases tapered core 780. Sleeve 740 and core 760 are made from a polymeric material, preferably nylon.

Figure 9:
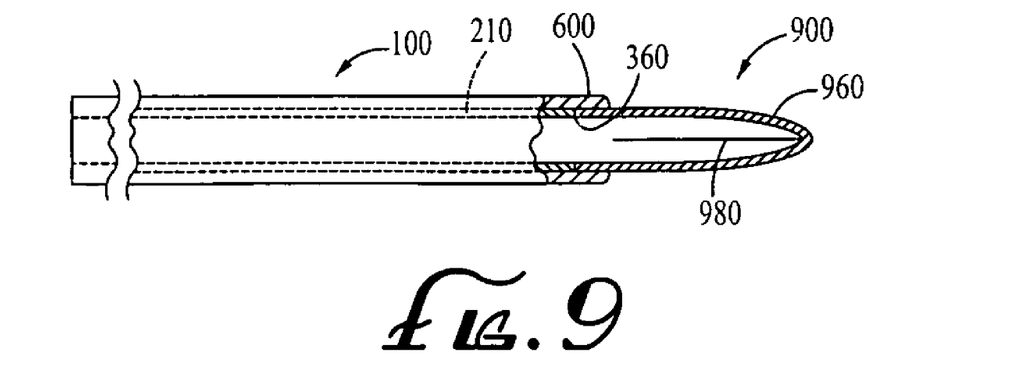

Referring to FIG. 9, in an alternative embodiment, distal tip portion 900 comprises a duck bill 960 bonded to sealing element 600 by, for example, a flexible adhesive, such as urethane. Duck bill 960 is fabricated from a polymeric material (e.g., PET, polyimide, or polyethylene) and includes a longitudinal slit 980 in opposite walls of distal tip portion 900. Longitudinal slit 980 is biased closed; however, upon an application of an internal force, such as, for example, fluid pressure or a longitudinal thrusting force, longitudinal slit 980 opens to provide a passageway through distal tip portion 900.

While various embodiments of the application have been described, it will be apparent to those of ordinary skill in the art that many more embodiments and implementations are possible that are within the scope of the subject invention. Accordingly, the invention is not to be restricted except in light of the attached claims and their equivalents.

What is claimed is:

1. A catheter system, comprising:
    a guiding catheter having a proximal end, a distal end, a lumen extending therebetween;
    an imaging catheter having an elongate tubular member with proximal and distal ends and a lumen extending therebetween, formed from a resin, wherein a proximal portion of the tubular member defines a pattern of slots generally angled at 45 degrees disposed at between 90 and 120 degree intervals;
    a cover tube laminated over the elongate tubular member; and
    a guidewire;
    wherein the imaging catheter and guidewire are simultaneously translatable through the lumen of the guiding catheter, and further wherein the imaging catheter and guidewire each have an axis, and the axes are positioned adjacent with respect to each other when located within the lumen of the guiding catheter.

2. The catheter system of claim 1, wherein the resin is selected from the group consisting of polyetheretherketon, polyimide, braided coiled composites and hypo tubes.

3. The catheter system of claim 1, wherein the cover tube is formed from a material selected from the group consisting of polyethylene, urethane and PEBAX™.

4. The catheter system of claim 1, wherein the outer diameter of the imaging catheter is less than about 0.044 inches.

5. The catheter system of claim 4, wherein the outer diameter of the guidewire is about 0.014 inches.

6. The catheter system of claim 1, further comprising an acoustic imaging window.

7. The catheter system of claim 6, wherein the acoustic imaging window is a rounded window attached at the distal end of the elongate tubular element.

8. The catheter system of claim 6 wherein the acoustic imaging window is formed from a material selected from the group consisting of methylpentene copolymer, polyethylene, urethane and PEBAX™.

9. The catheter system of claim 6, wherein the acoustic imaging window is located at a distal tubular portion of the imaging catheter, proximal from a distal tip of the imaging catheter.

10. The catheter system of claim 1, wherein the acoustic imaging window is attached to the cover tube at a common joint.

11. The catheter system of claim 10, wherein acoustic imaging window is attached to the cover tube using a low profile thermal bond.

12. The catheter system of claim 1, further comprising a rotatable imaging core adapted to pass through the lumen of the imaging catheter, the imaging core including a flexible drive-shaft and a transducer element.

13. The catheter system of claim 12, wherein the imaging core further includes a transducer housing that attaches the transducer to the drive-shaft.

14. The catheter system of claim 13, wherein the transducer housing has a cut-away portion which slopes at an angle with respect to the central axis of the drive-shaft.

15. The catheter system of claim 1, wherein the imaging catheter has a proximal portion comprised of a flexible section with an angled slot.

16. The catheter system of claim 15, wherein the slot extends continuously through at least two rotations.

17. The catheter system of claim 16, wherein the width of the slot varies along the length of the slot whereby the width of the proximal slots is less than the width of the distal slots.

18. The catheter system of claim 15, wherein the proximal portion is comprised of a flexible section having a groove, which partially cuts through the flexible section.

19. The catheter system of claim 15, wherein the acoustic imaging window is located at a distal tubular portion of the imaging catheter, proximal from a distal tip of the imaging catheter, and the proximal portion includes a transition section located proximally of the flexible section, the transition section having portions of the wall removed to impart an intermediate range of flexibility such that the transition section is less flexible than the flexible section.

20. The catheter system of claim 19, wherein the transition section includes at least one slot shorter than a slot of the flexible section.

21. The catheter system of claim 15, wherein the distal tip has a tapered distal extremity for atraumatic insertion into the body.

22. The catheter system of claim 15, wherein the distal tip has a duck bill extremity for atraumatic insertion into the body.

23. The catheter system of claim 15, wherein the acoustic imaging window is located at a distal tubular portion of the imaging catheter, proximal from a distal tip of the imaging catheter, and the proximal portion is made from nitinol.

24. The catheter system of claim 1, wherein the imaging catheter includes a distal tip having a guidewire port and guidewire lumen dimensioned for the passage of the guidewire.

* * * * *